(12) United States Patent
Campbell et al.

(10) Patent No.: US 6,375,637 B1
(45) Date of Patent: Apr. 23, 2002

(54) CATHETER BALLOON HAVING A CONTROLLED FAILURE MECHANISM

(75) Inventors: Carey V. Campbell; Alvaro J. Laguna, both of Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 09/384,903

(22) Filed: Aug. 27, 1999

(51) Int. Cl.[7] ............................................. A61M 29/00
(52) U.S. Cl. .................. 604/103; 604/96.01; 604/247; 604/537; 606/194
(58) Field of Search .................. 604/96.01, 99.01, 604/103, 103.01, 103.05, 103.06, 103.1, 103.14, 246, 247, 256, 523, 537; 606/194, 192; 250/149.8, 343

(56) References Cited

U.S. PATENT DOCUMENTS

| | | | |
|---|---|---|---|
| 2,813,531 A | 11/1957 | Lee | |
| 3,726,283 A | 4/1973 | Dye et al. ............. | 128/349 BV |
| 4,003,382 A | 1/1977 | Dyke | |
| 4,088,135 A | 5/1978 | O'Neill | |
| 4,301,803 A | 11/1981 | Handa et al. | |
| 4,406,653 A | 9/1983 | Nunez | |
| 4,757,194 A * | 7/1988 | Simms et al. ............... | 250/227 |
| 4,857,054 A | 8/1989 | Helfer ......................... | 604/102 |
| 5,007,919 A | 4/1991 | Silva et al. | |
| 5,035,705 A | 7/1991 | Burns ......................... | 606/194 |
| 5,066,298 A | 11/1991 | Hess ............................ | 606/194 |
| 5,078,681 A | 1/1992 | Kawashima | |
| 5,085,636 A | 2/1992 | Burns ......................... | 604/99 |
| 5,100,385 A | 3/1992 | Bromander .................. | 604/99 |
| 5,197,952 A * | 3/1993 | Marcadis et al. ............. | 604/96 |
| 5,221,258 A | 6/1993 | Shturman | |
| 5,236,659 A | 8/1993 | Pinchuk et al. | |
| 5,318,587 A | 6/1994 | Davey | |
| 5,370,617 A | 12/1994 | Sahota | |
| 5,385,548 A * | 1/1995 | Williams et al. ............... | 604/96 |
| 5,391,148 A | 2/1995 | Bonis | |
| 5,454,788 A | 10/1995 | Walker et al. ................ | 604/96 |
| 5,591,129 A * | 1/1997 | Shoup et al. ................. | 604/96 |
| 5,649,908 A | 7/1997 | Itoh | |
| 5,714,110 A | 2/1998 | Wang et al. | |
| 5,792,118 A | 8/1998 | Kurth et al. ................. | 604/246 |
| 5,807,328 A | 9/1998 | Briscoe ........................ | 604/96 |
| 6,033,379 A * | 3/2000 | Barra et al. .................... | 604/96 |
| 6,203,558 B1 | 3/2001 | Dusbabek et al. .......... | 606/198 |

FOREIGN PATENT DOCUMENTS

EP        768097        4/1997

* cited by examiner

*Primary Examiner*—Angela D Sykes
*Assistant Examiner*—Cris Rodriguez
(74) *Attorney, Agent, or Firm*—Wayne D. House

(57) ABSTRACT

A catheter balloon having a controlled failure mechanism such that release of pressure contained within the balloon occurs in a controlled fashion when a predetermined inflation pressure in excess of normal operating pressure is reached within the balloon. The failure mechanism is the result of incorporating a failure mechanism into at least one end of the balloon, for example, with a controlled amount of attachment of the at least one end to the catheter shaft. This end of the balloon therefore fails at a predetermined pressure with the failure occurring before catastrophic failure of the balloon by rupture between the balloon ends. The controlled failure mechanism allows for non-catastrophic failure such that the balloon remains intact following failure and remains easily withdrawable from the body conduit into which it has been inserted.

30 Claims, 5 Drawing Sheets

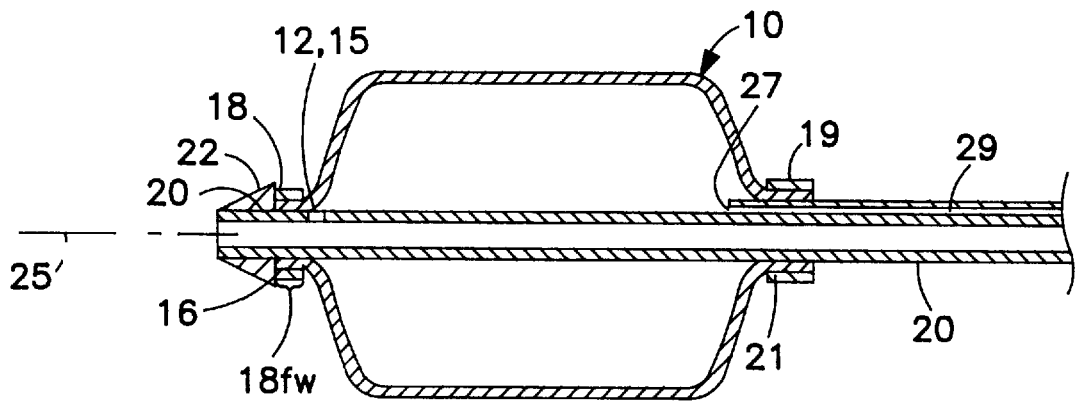
FIG. IE
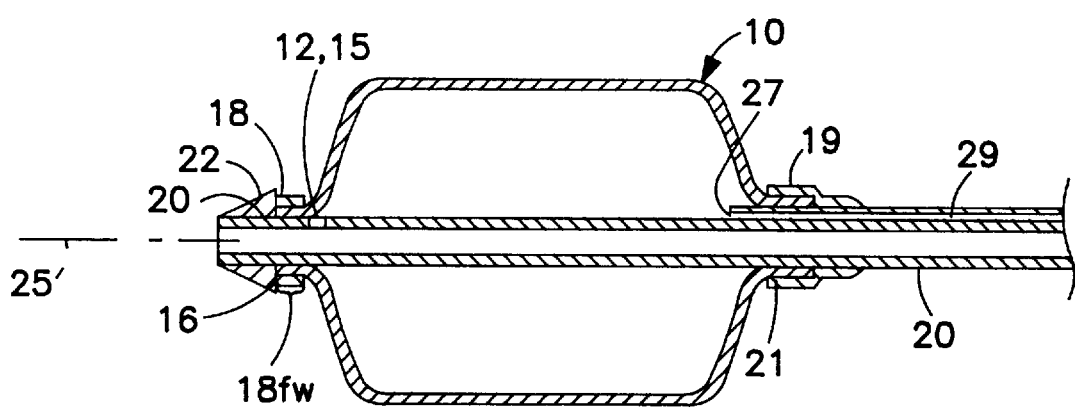
FIG. IF
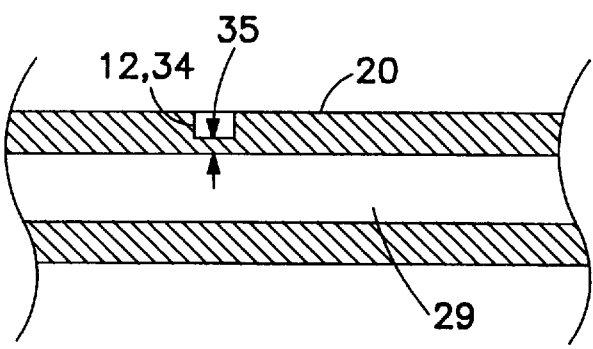
FIG. IG

CATHETER BALLOON HAVING A CONTROLLED FAILURE MECHANISM

FIELD OF THE INVENTION

The present invention relates to the field of balloon catheters and more particularly to catheter balloons having controlled failure mechanisms for the prevention of catastrophic failure of the balloon during overpressure conditions.

BACKGROUND OF THE INVENTION

Balloon catheters are used for a variety of medical procedures. Their conventional use entails the insertion of the balloon catheter into a body conduit at a cannulation site and pushing the length of the catheter progressively into the body conduit until the balloon located at the distal end of the balloon catheter reaches the desired site. The balloon is then inflated at that site in order to implement the desired therapy. The body conduit is most often a blood vessel and more particularly an artery, although balloons are used within a variety of other body conduits such as, for example, bile ducts. The inflation of the balloon may be used for various therapeutical reasons such as causing temporary occlusion of the body conduit, for the delivery of a medicant to the specific site of inflation, to disrupt plaque or thrombus or to deliver a device to a desired site within the body conduit. Devices most commonly delivered with a catheter balloon include vascular stents, vascular stents in combination with vascular grafts (stent-grafts), and intraluminal vascular grafts, all of which may be circumferentially distended by inflation of the balloon until the device is implanted in firm contact with the wall of the body conduit.

In use, catheter balloons are known to occasionally rupture due to inflation to higher than design pressures. Sudden rupture and corresponding sudden release of inflation pressure has resulted in damage to the surrounding body conduit. Even if the balloon remains intact following rupture the configuration of the damaged balloon may make withdrawal of the balloon from the body conduit quite difficult. These occasional ruptures can also result in fragmentation of the balloon and the necessity to retrieve the fragments. Due to displacement of the fragments distally as a result of fluid flow through the body conduit, retrieval is difficult at best and may require interventional surgery. It may not be possible to know with certainty that all pieces have been retrieved.

Provision for the rupturing of catheter balloons is known. U.S. Pat. No. 5,221,258 to Shturman teaches a catheter balloon having a longitudinal segment of weakness intended to allow the intentional rupture of the balloon between its ends in order to release a device contained within the balloon. Shturman also describes that the balloon may be provided with a portion of larger diameter than the remainder of the balloon in order that the higher hoop stress in the larger diameter portion results in rupture, again in order to release a device contained within the balloon.

SUMMARY OF THE INVENTION

Catheter balloons of various different designs have different normal operating pressures which are not intended by the manufacturer to be exceeded. If these normal operating pressures are exceeded by more than the amount of safety margin designed into a particular balloon, then the balloon is liable to rupture between the balloon ends. This amount of pressure required to result in failure by rupture is commonly referred to as the burst or rupture pressure. Rupture may result in fragmentation of the balloon with the fragments being difficult or impossible to recover, potentially leading to serious health problems for the patient. Likewise, failure by rupture can result in the damaged balloon being very difficult to remove due to the balloon material dragging on the vessel walls. Rupture may also result in improper deployment of a device being delivered by the balloon, requiring removal of both the device and the damaged balloon. All of these types of failure may be considered to be catastrophic.

The balloon catheter of the present invention provides for non-catastrophic failure by means other than rupture. This is accomplished by allowing an end attachment of one end of the balloon to fail by any of various means at a predetermined inflation pressure that is between the normal maximum operating pressure and the burst pressure. The predetermined pressure is not required to be a precise specific inflation pressure but may be a range extending for any portion of the range of pressure between the normal maximum operating pressure and the burst pressure.

The present invention thus relates to a catheter balloon having a controlled failure mechanism such that release of inflation pressure contained within the balloon occurs in a controlled fashion when a predetermined pressure is exceeded within the balloon. The controlled failure is the result of incorporating a failure mechanism into at least one end of the balloon (e.g., with a controlled amount of attachment of the balloon end to the catheter shaft). The result, as described above, is that the attachment of the at least one end fails at a predetermined pressure with the failure occurring before catastrophic rupture of the balloon between its attached ends. The end having the controlled failure mechanism may be either the distal end (leading end) or the proximal end (trailing end). Regardless of which end is made to be weaker resulting in failure of that end, the balloon remains intact and is not separated from the catheter shaft following failure, and is therefore easily withdrawable without loss of fragments within the body conduit.

Alternatively, both ends of the balloon may be provided with the controlled failure mechanism if there is no reason to limit failure to a particular end. With failure occurring at either end, the balloon remains intact and joined to the catheter shaft, and easily withdrawable from the body conduit into which it has been inserted.

The controlled failure mechanism is most preferably restricted to the balloon ends in the region of the attachment of the balloon end to the exterior surface of the catheter shaft. In normal operation below the predetermined controlled failure pressure, the controlled failure mechanism does not extend into the region of the balloon between the attached ends that is directly exposed to the fluid used to supply the inflation pressure. In this way, uncontrolled rupture of the balloon between the attached ends is avoided. With increasing pressure leading ultimately to the predetermined pressure at which it is desired to cause failure in a controlled manner, the stress on the balloon end attachments to the exterior surface increases and is utilized to provide the balloon failure in a controlled manner at the attachment site.

For purposes of the present invention, the balloon ends (or end attachments) are the end portions of the balloon which are affixed to the catheter shaft by any suitable method. During normal use, the ends of the balloon are not directly exposed to the inflating medium (such as a saline fluid) used to supply inflation pressure to the interior of the balloon between the opposing ends.

Various embodiments entail the provision of at least one aperture or slit at least partially through the thickness of the balloon material in at least one end region of the balloon where it is secured to the exterior of the catheter shaft. Excess pressure results in progressive failure of the end attachment with the result that the inflation pressure is relieved through exposure of at least a portion of the aperture or slit. Two or more slits located at one end of the balloon may be used. This arrangement allows for one side of the end of the balloon (between the slits) to come free from its attachment to the catheter shaft. The result is the release of the balloon pressure in a controlled and more gradual manner than would be the case with conventional catastrophic rupture, while maintaining the integrity of the remainder of the balloon in order that the failed balloon catheter is easily removed in its entirety.

It is apparent that the various methods of providing the controlled failure mechanism for specific balloon designs in order to achieve failure at desired predetermined pressures will require engineering with regard to all construction aspects of the balloon catheter. These aspects include materials selection, number of layers provided, method of attachment of the balloon to the catheter shaft, and various dimensions. They also include the possibility of controlling the rate and direction of fluid flow following the controlled failure, by the use of failure mechanisms such as the various types described herein. Such engineering is within the capability of ordinary skill in the art.

The design of catheter balloons and the use of reliable materials have resulted in a state of development at which it is possible to predict the failure of a balloon by rupture with some accuracy. With the controlled failure mechanism of the present invention, it is also possible to reliably cause failure to occur in a non-catastrophic manner at a predetermined pressure which is less than the pressure at which the balloon could be anticipated to rupture catastrophically.

A preferred balloon for use with the failure mechanism of the present invention is described by U.S. Pat. Nos. 5,752,934 and 5,868,704 to Campbell et al., incorporated by reference herein. These patents teach the construction of a composite balloon preferably made from porous expanded polytetrafluoroethylene (hereinafter ePTFE) and an elastomeric material such as silicone or polyurethane. As further described by these patents, the ends of the composite balloon are preferably secured to the exterior surface of a catheter shaft using a wrapping of a narrow tape of ePTFE film retained by an adhesive such as cyanoacrylate adhesive. The manufacture of ePTFE, including the films from which the composite balloon is manufactured and which are also used to secure the balloon ends to the catheter shaft are made, is taught by U.S. Pat. Nos. 3,953,566 and 4,187,390 to Gore. These patents are also incorporated by reference herein.

BRIEF DESCRIPTION OF THE DRAWINGS

FIGS. 1D and 1E are longitudinal cross sections of alternative embodiments to the catheter balloon described by (respectively) FIGS. 1B and 1C.

FIG. 1F is a longitudinal cross section of an alternative embodiment wherein a securing band is provided of adequate width to allow it to cover both the balloon end and the adjacent portion of the catheter shaft to which the balloon end is secured.

FIG. 1G is a longitudinal cross section of a portion of a catheter shaft incorporating an alternative aperture controlled failure mechanism wherein the aperture is a blind aperture extending partly through the wall of the catheter shaft.

DETAILED DESCRIPTION OF THE INVENTION

Figure 1:
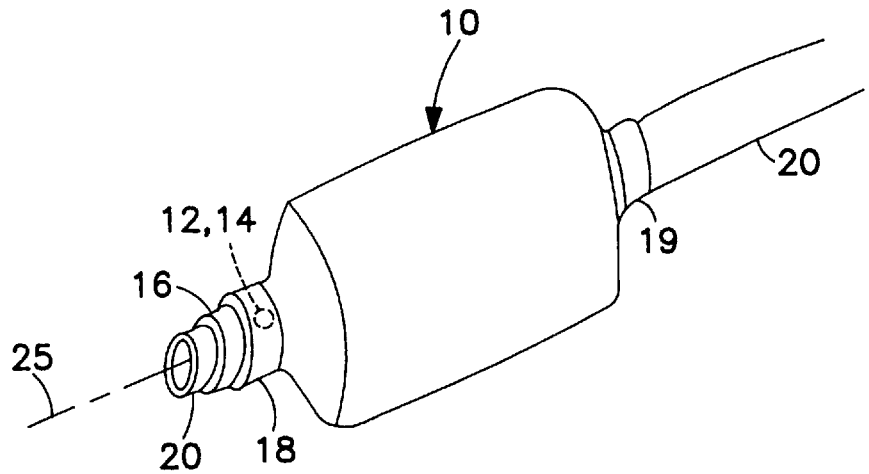
FIG. 1 is an isometric view of a catheter balloon of the present invention having a controlled failure mechanism in the form of an aperture through the wall of the balloon in the region of the attachment of the balloon end to the exterior surface of the catheter shaft, the aperture being located at the distal end of the balloon beneath a binding or securing band used to secure the distal end of the balloon to the exterior surface of the catheter shaft.

FIG. 1 is an isometric view of a catheter balloon 10 of the present invention having a controlled failure mechanism 12 in the form of an aperture 14 through the wall of the balloon 10. While the aperture 14 is shown to be of round shape, it is apparent that any shape might be used to include round, oval, square, triangular, etc. The aperture 14 is shown located at the distal end 16 of the balloon 10. Distal end 16 constitutes the portion of the balloon 10 that is joined or affixed to the surface of the catheter shaft, i.e., the end attachment portion of the balloon. It is apparent that the end attachment portion of the balloon (e.g., distal end 16), being affixed to the surface of the catheter shaft, is not during normal use directly exposed to the inflating medium that is used to inflate the balloon. Preferably, as shown by FIG. 1, a binding or securing band 18 is used to secure the distal end 16 of the balloon 10 to the exterior surface of the catheter shaft 20. A similar binding or securing band 19 retains the proximal end of the balloon 10 to the exterior surface of the catheter shaft 20.

The aperture 14, while shown by FIG. 1 only at the distal end 16 of the balloon 10, may be alternatively located at the proximal end or at both ends of the balloon.

Aperture 14 may also be two or more apertures located through the balloon material beneath the securing band 18. Multiple apertures may be used, to include the portion of balloon material located beneath the securing band being porous through its thickness and therefore having a multiplicity of apertures. This may be accomplished in various ways. For example, for a balloon material comprising a porous layer provided with a non-porous coating (as taught by U.S. Pat. Nos. 5,752,934 and 5,868,704), the coating layer may be removed by any expedient means in the area of the balloon material attached to the catheter shaft 20 and which will be covered by a securing band 18. Such a porous area may have the advantage of reducing the rate of escape of the inflating medium upon failure.

The catheter shaft 20 is shown with corresponding longitudinal axis 25. Shaft 20 may be made from a variety of materials well known in the art including PTFE, PET (polyethylene terephthalate), PE (polyethylene), an amide-based thermoplastic elastomer such as PEBA, and various composites. The shaft is generally a tubular construction and contains at least one passageway extending between the distal and proximal ends of the balloon catheter that allows for passage of an inflating medium such as a saline fluid. The catheter shaft will most generally contain at least one additional passageway that allows for passage of, for example; a guidewire device.

The balloon 10 may be virtually any type of known catheter balloon including relatively compliant balloons made from materials such as latex and relatively non-compliant balloons made from materials such as PET. The balloon may also be a composite balloon such as the balloon made as taught by U.S. Pat. Nos. 5,752,934 and 5,868,704 to Campbell et al.

While the securing bands 18 and 19 may be of various forms and materials (e.g., various elastomeric materials of suitable durometer or various non-elastomeric materials designed to yield at a suitable predetermined inflation pressure). A preferred securing band is one taught by the Campbell et al. patents in the form of a wrapping of a narrow strip of ePTFE film about the ends of the balloon which are to be joined to the exterior surface of the catheter shaft. These strong, thin and porous films are secured by an adhesive such as a cyanoacrylate which is capable of adhering well to the exterior surface of the balloon and also penetrates the void space of the narrow strip of porous ePTFE film used as a securing binding. A preferred adhesive is Loctite part no. 4981. Other adhesives are also believed to be suitable including various silicones, polyurethanes and epoxies.

Figure 1A:
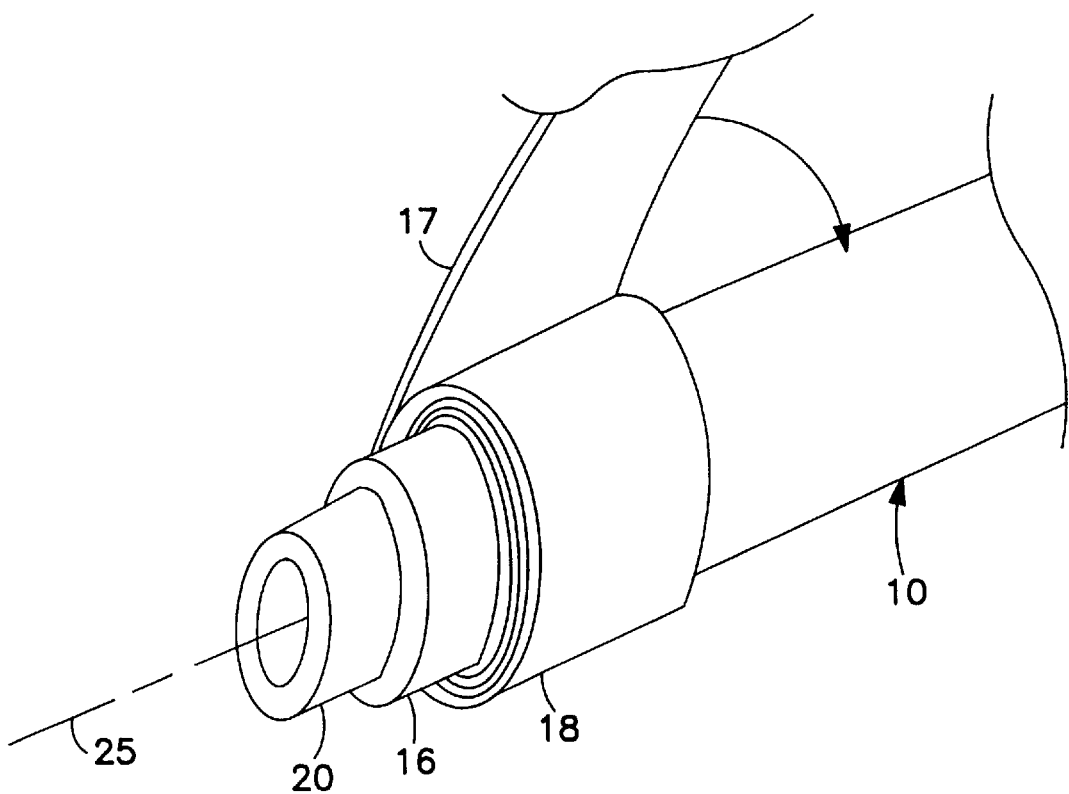
FIG. 1A describes an enlarged isometric view of an end of the balloon showing a securing band being applied to the distal end of the balloon in the form of a wrapping of, for example, ePTFE film.

FIG. 1A shows an enlarged isometric view of the distal end of the catheter balloon of the present invention also shown in FIG. 1, wherein according to FIG. 1A the securing band 18 is being applied to the distal end 16 of the uninflated balloon 10 in the form of a wrapping of the thin strip of ePTFE film 17. Immediately prior to beginning this film wrapping of the exterior surface of the end of the balloon, a thin coating of the selected adhesive is applied to that exterior surface. The wrapping of the ePTFE film is then applied with tension on the film adequate to ensure that the wrapping when complete is tight against the exterior surface of the balloon end. The adhesive permeates the void space of the ePTFE film during the wrapping process.

It is apparent that the same or similar type of wrapping may be used to create a securing band on either or both the distal and proximal ends of the catheter balloon.

The same type of adhesive can be used between the exterior surface of the catheter shaft and the interior surface of the end of the balloon. The exterior surface of the catheter shaft, the balloon end and the securing binding may all be adhered together at the same time, or alternatively the securing band may be adhered in a separate step following joining of the balloon end to the catheter shaft.

Figure 1B:
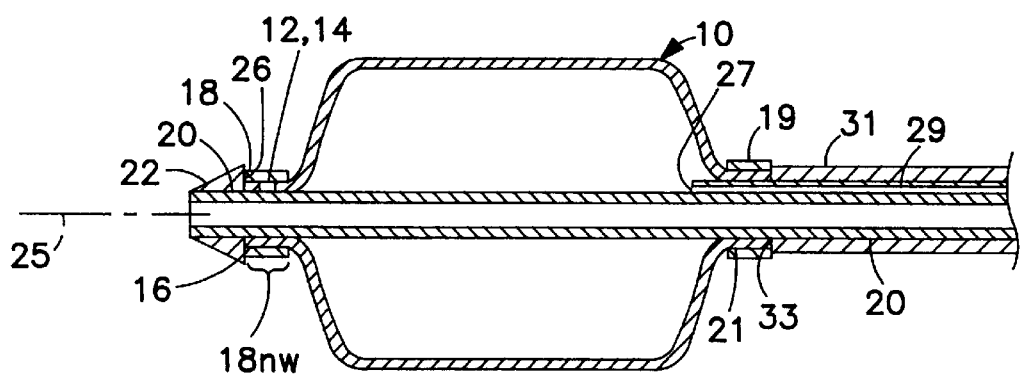
FIG. 1B is a longitudinal cross section of the catheter balloon of FIG. 1.

FIG. 1B is a longitudinal cross section of the embodiment shown isometrically by FIG. 1. Inflation port 27 is intended as representative of various known inflation means for conveying into balloon 10 any pressurizing medium such as saline liquid conveyed to port 27 via a connecting channel 29 within the catheter shaft 20. Optional conical catheter tip 22, used conventionally for ease of insertion of the catheter into a body conduit, is shown in the longitudinal cross sections of FIG. 1B and 1C and is omitted from other figures for clarity. The larger diameter end of the conical tip 22 (the end adjacent to the distal end 16 of balloon 10) may be conveniently used to provide a distal stop 26 against distal end 16 of balloon 10 and against which the securing band 18 may be applied.

Catheter shaft 20 may optionally be provided with extra outer jacket 31 which coaxially encloses shaft 20. Extra outer jacket 31 ends against the proximal end 21 of balloon 10 and proximal securing band 19. Outer jacket 31 thus provides a stop 33 against the proximal end 21 of the balloon 10 and the proximal securing band 19. This same function may also be provided in an alternative manner (not specifically shown) by the use of a thicker wall catheter shaft 20 which is stepped down in diameter where the proximal end 21 of the balloon 10 is affixed to its outer surface. This is the equivalent of providing outer jacket 31 and catheter shaft 20 in the form of a single component that also provides a stop 33 against the proximal end 21 of the balloon 10 and the proximal securing band 19 in the same manner as the two-piece construction shown by FIG. 1B.

During an overpressure condition, it is anticipated that the force exerted on the securing band 18 will increase until failure commences by the band 18 beginning to be pushed away axially from distal end 16 of the balloon 10 (toward tip 22). As shown by the longitudinal cross section of Figure lC, this continues until the aperture 14 is exposed from its previous location entirely beneath the securing band 18, with the result that the pressure contained within the balloon 10 is released through aperture 14. The securing band 18 remains affixed to the distal end 16 of the balloon 10. The size of the aperture 14 is such that the pressure is released in a relatively gradual manner without catastrophic consequences. The balloon remains intact and easily withdrawn from within the body conduit.

Figure 1C:
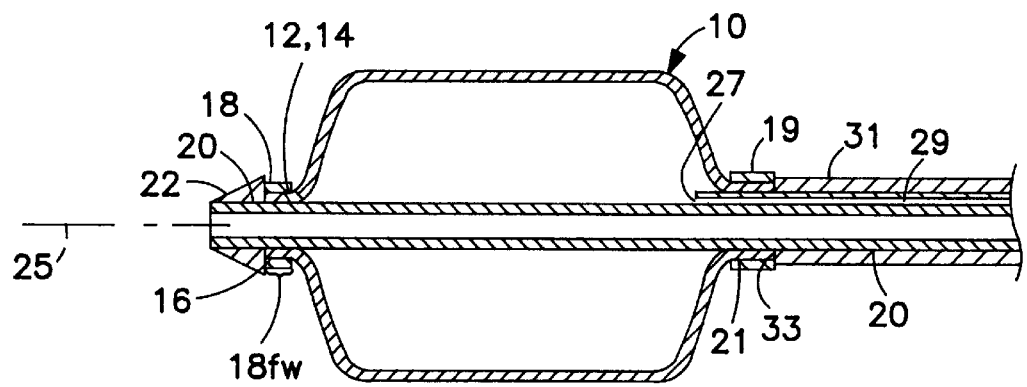
FIG. 1C is a longitudinal cross section of the catheter balloon of FIGS. 1 and 1B during controlled failure and release of inflation pressure resulting from inflation pressure reaching the predetermined value necessary to cause the failure.

As also shown by the longitudinal cross sections of FIGS. 1B and 1C, an advantage of a securing band 18 made from a wrapping of a narrow ePTFE film, adhered to the underlying end of the balloon, is that the securing band 18 is capable of narrowing in width under axial compression. The result is that as the balloon reaches the predetermined failure pressure and begins to exert the necessary force against the securing band 18 to activate the controlled failure mechanism 12 (e.g., the aperture 14 through the distal end 16 of the balloon 10). The securing band 18 narrows from normal width 18*nw* (FIG. 1B) to failure width 18*fw* (FIG. 1C) due to the compressive force exerted by the balloon in an axial direction (parallel to the longitudinal axis 25 of the catheter shaft 20). The narrowing of the securing band 18 to failure width 18*fw* results in aperture 14 being uncovered by the force exerted by excess pressure within the balloon 10, thereby allowing release of pressure through the exposed aperture 14. The portion of the securing band 18 adhered to the distal end 16 of the balloon 10 opposite the inflated end of the balloon remains effectively adhered to the distal end 16 of the balloon 10. The failure mechanism 12 is thus activated without loss of the securing band 18 from its fixation to the distal end 16 of balloon 10. Band 18 is further constrained by tip 22.

While ePTFE films are preferred for the securing band to enable the narrowing of the band under increasing balloon pressure, it is believed that other porous films (e.g., porous polypropylene) may be used as well. Likewise, non-porous films may be used as well if narrowing of the securing band is allowed to occur by wrinkling of the film and/or increasing loss of adhesion of the film to the underlying balloon material resulting from increasing balloon pressure applying increasingly greater force against the securing band.

The size of the one or more apertures 14 and the proximity of apertures to the distal end 16 of the inflated balloon 10 will be required to be engineered along with the remainder of the balloon design. This includes the balloon type and material as well as the material and design of the securing bands 18 and 19 and any adhesive used with those bands.

In order to ensure that failure begins at a particular end if that is desired, for example at the distal securing band 18 rather than at the proximal securing band 19, the proximal securing band 19 should be made to provide greater attachment security than the distal securing band 18. This may be accomplished by various methods including the use of a wider or thicker material for proximal securing band 19. More specifically, this may also be accomplished with the use of more wraps of ePTFE film, the use of stronger ePTFE film, the use of greater tension during film wrapping, or the use of a wider strip of ePTFE film, or any combination of any of these. Generally, any desired method may be used which provides for greater attachment security at one end than the other, with the attachment of the weaker end designed to fail at a predetermined inflation pressure.

Alternatively, as noted above, it may be more desirable to provide the failure mechanism 12 at both the distal end 16 and proximal end 21 of the balloon 10 for maximum reliability.

Figure 1D:
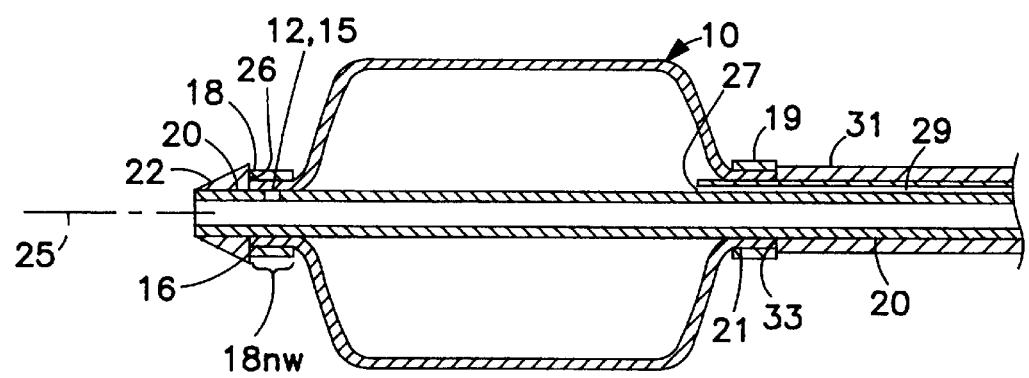

Another alternative to the controlled failure mechanism 12 in the form of aperture 14 shown by FIGS. 1B and 1C, is aperture 15 through the wall of catheter shaft 20 in the region of the distal end 16 of balloon 10. This alternative is shown by the longitudinal cross sections of FIGS. 1D and 1E. FIG. 1D shows balloon 10 inflated during normal operation within the normal balloon operating pressure while FIG. 1E shows balloon 10 exceeding the maximum normal operating pressure, having reached the predetermined pressure necessary to activate the controlled failure mechanism 12. In a similar manner to that shown by FIG. 1C, FIG. 1E shows that the predetermined pressure results in axial compression and narrowing of securing band 18 to failure width 18*fw*, thereby allowing the pressure contained within balloon 10 to escape via the now-uncovered aperture 15.

FIG. 1F is a longitudinal cross section of an alternative embodiment wherein a securing band 19 is provided of adequate width to allow it to cover both the balloon end 21 and the adjacent portion of the catheter shaft to which the balloon end is secured. In the example shown by this figure, the proximal end of the catheter is secured in such a manner although it is apparent that this technique can be used on either or both balloon ends depending on the desired balloon catheter construction.

FIG. 1G shows a longitudinal cross section of catheter shaft 20, without the optional extra outer jacket 31 of FIG. 1B. This represents still another alternative controlled failure mechanism 12 wherein a blind hole or aperture 34 is provided partially through the wall of the catheter shaft 20 at a selected location along the length of shaft 20. The location is selected such that the excess pressure contained within balloon 10 may be safely released. The blind hole 34 results in a local thinning of the wall of the catheter shaft, providing a point of weakness having a wall thickness 35 designed to rupture locally at the predetermined failure pressure. The blind hole 34 may be located within a portion of catheter shaft 20 extending within balloon 10 (i.e., between the balloon ends). Alternatively, it may be provided at another location along the length of the catheter shaft 20 that results in a weakening of the wall of the shaft 20 that contains the pressure supplied to balloon 10 by connecting channel 29.

Figure 2:
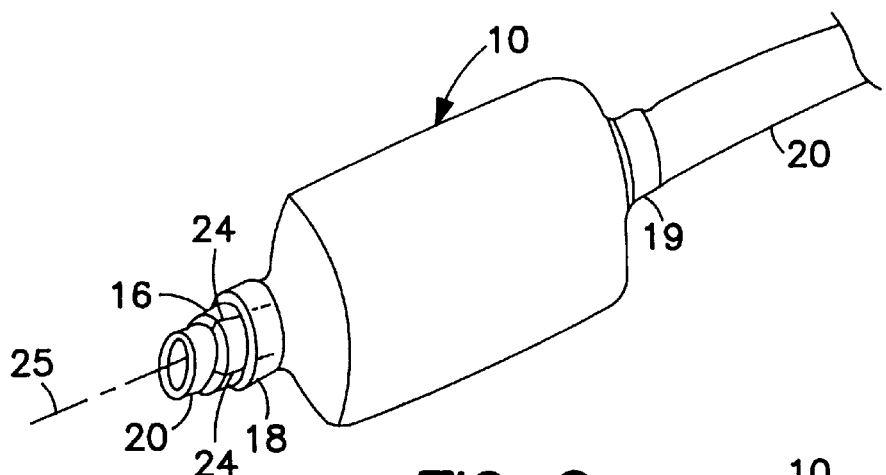
FIG. 2 is an isometric view of an alternative embodiment of the inventive balloon showing a preferred failure mechanism in the form of one or more slits (two are specifically shown) at one end of the balloon in the region which is intended to be secured to the catheter.

FIG. 2 is an isometric view of an alternative embodiment of the inventive balloon showing a preferred failure mechanism in the form of one or more slits 24 (two are specifically shown) at one end of the balloon 10 in the end attachment region that is secured to the exterior surface of the catheter shaft 20. The distal end 16 of the balloon 10 is provided with slits 24 in the embodiment shown by FIG. 2. Alternatively, the slits 24 may be provided at the proximal end 21 or at both the distal end 16 and proximal end 21 as desired. Slits 24 are preferably through the entire thickness of the material comprising the end of the balloon 10 and extend for a length beginning at the extreme end of the balloon back under the securing band 18 for a distance less than the full width of the band 18. Alternatively, the slits 24 may extend through only a portion of the thickness of the distal end 16 of the balloon 10 as long as they provide the necessary local weakness necessary to ensure controlled failure at the desired pressure.

Figure 2A:
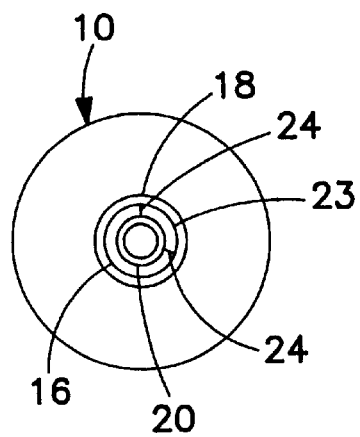
FIG. 2A is a distal end view of the catheter of FIG. 2.

As shown by the distal end view of FIG. 2A, slits 24 preferably extend entirely through the thickness of the distal end 16 of the balloon 10. While a single slit 24 may be adequate to achieve appropriate failure, two or more slits may also be used. They may be arranged to be 180 degrees apart or, as shown, they may be placed closer together rather than being equally disposed. Failure can result from securing band 18 being pushed axially back over the end of a slit 24 adjacent the inflated balloon 10 until a portion of the slit 24 is exposed from under the securing band 18, allowing the release of pressure. This is analogous to the failure described by FIG. 1B except that a portion of the slit 24 rather than the aperture 14 is exposed.

Figure 2B:
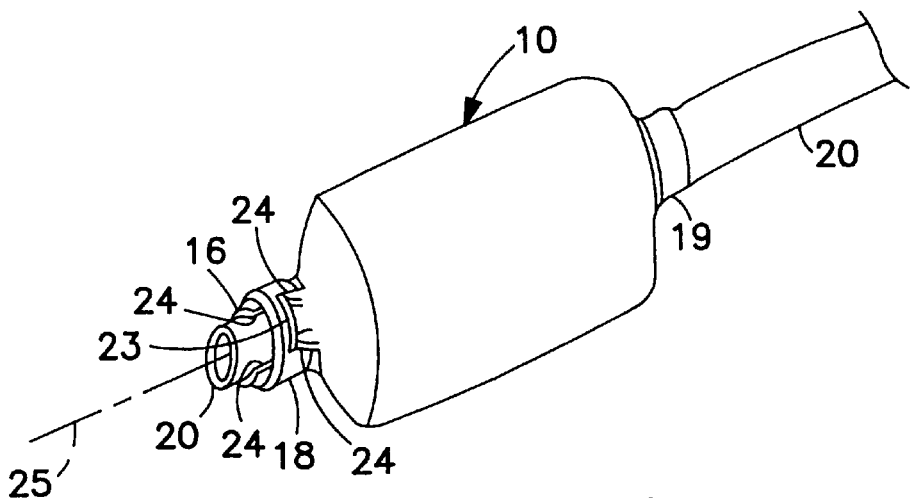
FIG. 2B is an isometric view of the balloon of FIGS. 2 and 2A showing one side of the slit end of the balloon becoming unattached from the catheter shaft during failure resulting from inflation pressure reaching a predetermined value necessary to cause the controlled failure.

FIG. 2B is an isometric view of the balloon of FIG. 2 showing one side of the slit end of the balloon becoming unattached from the catheter shaft during failure due to overpressure. The use of at least two slits 24 allows failure to occur by the portion 23 of the balloon material between the adjacent slits 24 being forced free from the securing band 18 and thereby releasing the pressure contained within the balloon 10. This type of failure may also be accomplished by the use of less adhesive or even no adhesive under flap portion 23.

Figure 3:
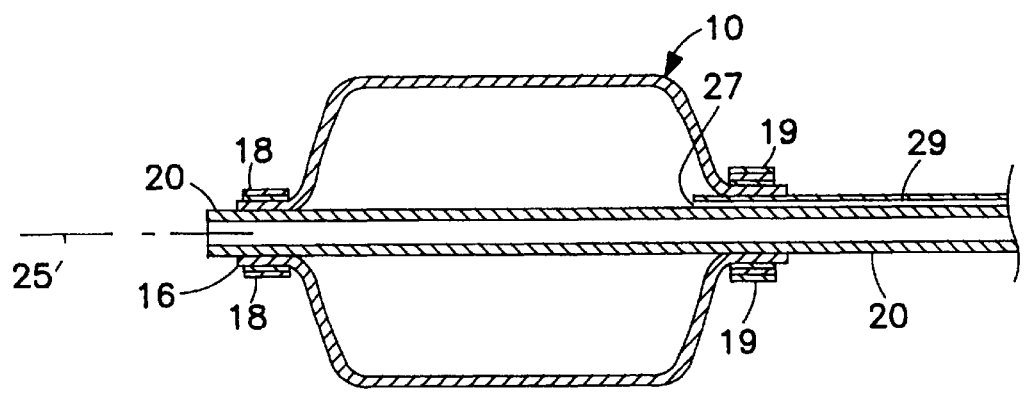
FIG. 3 is a longitudinal cross sectional view of another embodiment of the inventive balloon wherein one end of the balloon is shown to be more strongly secured to the exterior surface of the catheter shaft than the opposing end (by the use of additional wrapping or securing band material).

FIG. 3 is a longitudinal cross sectional view of another embodiment of the inventive balloon wherein one end of the balloon is shown to be more strongly secured to the exterior surface of the catheter shaft (by the use of additional wrapping or securing band material) than the opposing end. While either end may be made stronger than the opposing end, FIG. 3 shows an embodiment wherein the proximal securing band 19 is of greater strength than the distal securing band 18 in order to predispose failure to the distal end. In this instance, two wraps are shown being used to secure the distal end 16 of the balloon while three are used to secure the proximal end 21. The figure is intended only as indicative of the difference in the quantity of material used for the respective securing bands 18 and 19. It is preferred that the weaker band be at least about 20 percent weaker than the band at the opposing end of the balloon. For narrow strips of ePTFE film used as the material for the securing bands, because this material is available in relatively thin forms (e.g., 0.01 mm thickness), numerous wraps may be provided to the respective ends, for example, 16 and 20 wraps.

Figure 4:
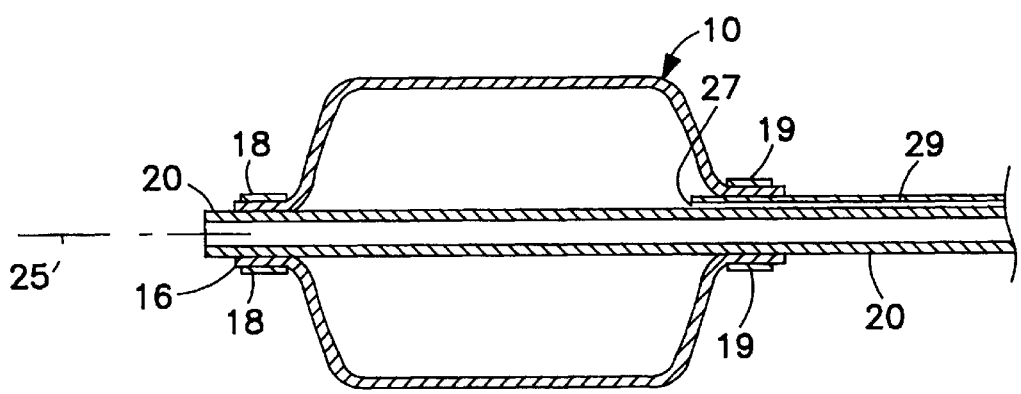
FIG. 4 is a longitudinal cross section of an alternative embodiment wherein a securing band of narrower width is used at one end of the balloon than at the opposite end.

Alternatively, the same result may be achieved by using a narrower securing band at one end of the balloon than at the other, as shown by the longitudinal cross section of FIG. 4.

Figure 5:
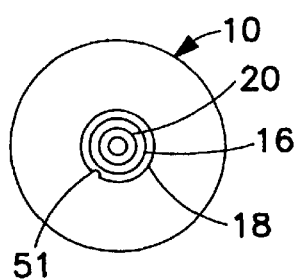
FIG. 5 is an end view of an alternative embodiment to that of FIG. 3 wherein a securing band at one end of the balloon is provided with a slit through a portion of the thickness of the band to allow it to fail before the band at the opposite end of the balloon which is not provided with such a slit.

FIG. 5 is an end view of an alternative to that of FIG. 3 wherein a securing band 18 at one end of the balloon (the distal end is shown) is provided with a slit 51 through a portion of the thickness of the band 18 to allow it to fail before the band 19 at the opposite end of the balloon which is not provided with such a slit. Variations of this include a slit across only a portion of the width of the securing band. During failure, the band splits at the location of the slit but remains adhered to the end of the balloon while no longer retaining pressure within the balloon. In still another variation, the securing band may be provided with an aperture through the band analogous to the aperture through the balloon end shown by FIG. 1. For all of these variations it is apparent that the material and dimensions of the securing band and the method of attachment of the securing band as well as the dimension and placement of any weakening slit or aperture will require engineering to achieve the desired pressure failure. Again, the weakened securing band may be provided at either or both ends of the balloon.

Figure 5A:
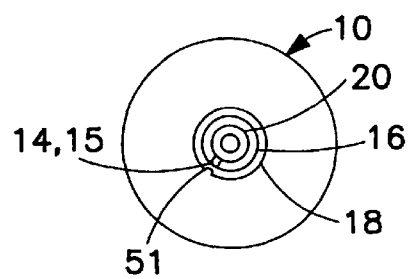
FIG. 5A is an alternative embodiment of the end view of FIG. 5 wherein the end of the balloon secured to the catheter shaft is provided with an aperture or point of weakness in some degree of alignment with a local point of weakness provided in the securing band.

FIG. 5A shows an alternative embodiment to that of FIG. 5 which adds the use of an aperture 14, 15 through the balloon end 16 that is aligned with the locally weakened securing band (slit 51).

While the principles of the invention have been made clear in the illustrative embodiments set forth herein, it will be obvious to those skilled in the art to make various modifications to the structure, arrangement, proportion, elements, materials and components used in the practice of the invention. For example, while the figures depict multi-lumen catheter shafts, the controlled failure mechanism may also be used on coaxially configured catheter shafts. To the extent that these various modifications do not depart from the spirit and scope of the appended claims, they are intended to be encompassed therein.

We claim:

1. A balloon catheter comprising an inflatable balloon having ends which are attached to a catheter shaft wherein at least one end is attached to the catheter shaft with a securing band and wherein a controlled failure mechanism is incorporated into the at least one end such that the at least one end fails due to an inflation pressure, resulting in loss of at least a portion of inflation pressure contained within the balloon, wherein the inflation pressure is less than a pressure required to rupture the balloon between the ends.

2. A balloon catheter according to claim 1 wherein the at least one end is a distal end.

3. A balloon catheter according to claim 1 wherein the at least one end is a proximal end.

4. A balloon catheter according to claim 1 wherein the securing band is axially compressible at the inflation pressure.

5. A balloon catheter according to claim 1 wherein the securing band comprises polytetrafluoroethylene.

6. A balloon catheter according to claim 5 wherein the securing band is axially compressible at the inflation pressure.

7. A balloon catheter according to claim 5 wherein the securing band comprises porous polytetrafluoroethylene.

8. A balloon catheter according to claim 7 wherein the porous polytetrafluoroethylene has void spaces at least partially filled with another material.

9. A balloon catheter according to claim 1 wherein the at least one end of the balloon includes at least one aperture therethrough.

10. A balloon catheter according to claim 9 wherein the securing band is axially compressible at the inflation pressure.

11. A balloon catheter according to claim 9 wherein the securing band comprises polytetrafluoroethylene.

12. A balloon catheter according to claim 11 wherein the securing band is axially compressible at the inflation pressure.

13. A balloon catheter according to claim 11 wherein the securing band comprises porous polytetrafluoroethylene.

14. A balloon catheter according to claim 13 wherein the porous polytetrafluoroethylene has void spaces at least partially filled with another material.

15. A balloon catheter according to claim 1 wherein the at least one end includes at least one slit at least partially therethrough.

16. A balloon catheter according to claim 15 wherein the securing band is axially compressible at the inflation pressure.

17. A balloon catheter according to claim 15 wherein the securing band comprises polytetrafluoroethylene.

18. A balloon catheter according to claim 17 wherein the securing band is axially compressible at the inflation pressure.

19. A balloon catheter according to claim 17 wherein the securing band comprises porous polytetrafluoroethylene.

20. A balloon catheter according to claim 19 wherein the porous polytetrafluoroethylene has void spaces at least partially filled with another material.

21. A balloon catheter according to claim 1 wherein the ends are secured to the catheter shaft by securing bands and wherein the at least one end has a weaker securing band.

22. A balloon catheter according to claim 21 wherein at least one securing band comprises polytetrafluoroethylene.

23. A balloon catheter according to claim 22 wherein the at least one securing band comprises porous polytetrafluoroethylene.

24. A balloon catheter according to claim 23 wherein the porous polytetrafluoroethylene has void spaces at least partially filled with another material.

25. A balloon catheter according to claim 21 wherein the weaker securing band is thinner.

26. A balloon catheter according to claim 21 wherein the weaker securing band has a local weakness.

27. A balloon catheter according to claim 21 wherein the weaker securing band of the at least one end is narrower.

28. A balloon catheter according to claim 1 wherein the controlled failure mechanism is incorporated into at least two ends.

29. A balloon catheter according to claim 1 wherein the at least one end includes at least two slits at least partially therethrough.

30. A balloon catheter according to claim 29 wherein a flap between the at least two slits is released from beneath the securing band at the inflation pressure.

* * * * *